(12) United States Patent
Magee et al.

(10) Patent No.: US 9,333,043 B2
(45) Date of Patent: May 10, 2016

(54) FETAL INTERVENTION USING MAGNETICALLY-GUIDED NAVIGATION

(71) Applicant: Fetal Care Consultants, LLC, Dallas, TX (US)

(72) Inventors: Kevin P. Magee, Dallas, TX (US); Alan W. Nugent, Dallas, TX (US)

(73) Assignee: Fetal Care Consultants, LLC, Dallas, TX (US)

( * ) Notice: Subject to any disclaimer, the term of this patent is extended or adjusted under 35 U.S.C. 154(b) by 329 days.

(21) Appl. No.: 14/199,993

(22) Filed: Mar. 6, 2014

(65) Prior Publication Data

US 2014/0276609 A1 Sep. 18, 2014

Related U.S. Application Data

(60) Provisional application No. 61/778,119, filed on Mar. 12, 2013.

(51) Int. Cl.
*A61B 34/00* (2016.01)
*A61B 19/00* (2006.01)
*A61M 25/01* (2006.01)

(52) U.S. Cl.
CPC ............ *A61B 19/2203* (2013.01); *A61B 34/73* (2016.02); *A61M 25/0127* (2013.01); *A61M 2210/145* (2013.01)

(58) Field of Classification Search
CPC .................... A61M 25/0127; A61M 25/0105; A61M 25/0133; A61M 25/08; A61M 2210/145; A61M 2210/1146; A61M 2025/0058; A61M 2025/1585; A61M 1/3659; A61B 34/73; A61B 2034/731–2034/733; A61B 2019/2253; A61B 2019/2257; A61B 2019/2261; A61B 2019/2265; A61B 17/34; A61B 17/3421; A61B 17/3423; A61B 19/2203
USPC .......... 606/167, 194, 192, 130; 604/509, 510, 604/95.01
See application file for complete search history.

(56) References Cited

U.S. PATENT DOCUMENTS

| | | | | |
|---|---|---|---|---|
| 4,777,951 | A | * 10/1988 | Cribier | A61M 25/0023 600/485 |
| 5,106,369 | A | * 4/1992 | Christmas | A61B 17/0218 604/506 |
| 5,654,864 | A | 8/1997 | Ritter et al. | |
| 6,311,082 | B1 | 10/2001 | Creighton et al. | |

(Continued)

OTHER PUBLICATIONS

McElhinney, Doff B. et al., "Current Status of Fetal Cardiac Intervention", Journal of the American Heart Association, 2010, Circulation 2010; 121:1256-1263, 9 pages.

*Primary Examiner* — Jonathan W Miles
*Assistant Examiner* — Majid Jamialahmadi
(74) *Attorney, Agent, or Firm* — R. Johnston Law, PLLC

(57) ABSTRACT

Methods and systems for fetal intervention to address malformations or other conditions are presented. In one instance, a method is provided that includes introducing a guide catheter into the fetus' venous system and using controlled magnets to position the guide catheter at a desired location. The method also involves positioning the treatment catheter at a treatment location using the guide catheter and delivering a treatment using the treatment catheter at the treatment location. In one particular application, a hypoplastic left heart is treated by using a balloon catheter as the treatment catheter and inflating a balloon on the balloon catheter at the aortic valve. Other methods and systems are disclosed.

15 Claims, 8 Drawing Sheets

(56) References Cited

U.S. PATENT DOCUMENTS

| | | |
|---|---|---|
| 6,315,709 B1 | 11/2001 | Garibaldi et al. |
| 6,330,467 B1 | 12/2001 | Creighton et al. |
| 2005/0148880 A1* | 7/2005 | Tower ............... A61B 17/12136 600/470 |
| 2007/0016131 A1* | 1/2007 | Munger ............ A61M 25/0127 604/95.05 |

\* cited by examiner

FETAL INTERVENTION USING MAGNETICALLY-GUIDED NAVIGATION

RELATED APPLICATIONS

This application claims the benefit of U.S. Provisional Application 61/778,119, filed on Mar. 12, 2013, entitled "Fetal Intervention Using Magnetically-Guided Catheter," which is incorporated herein in its entirety by reference for all purposes.

FIELD

The present disclosure relates generally to care of fetuses in utero, and more particularly, but not by way of limitation, to fetal intervention using magnetically-guided navigation.

BACKGROUND

Congenital anomalies remain one of the leading causes of infant death in the United States. Approximately one percent of babies are born with congenital heart malformations. Approximately a third of those require surgery within the first year after birth. Subsequent surgeries are often needed as well, and mortality increases with each surgery.

SUMMARY

According to an illustrative embodiment of the invention, a method for addressing a fetal malformation in a fetus in utero through fetal intervention includes using a needle to access the fetus' umbilical cord or more generally venous system, providing a guide catheter having a magnetic object coupled at a distal end of the guide catheter, and positioning the guide catheter into the venous system of the fetus through the needle. The method further includes providing a plurality of controlled magnets operable to guide the magnetic object on the guide catheter in three dimensions to within at least a centimeter and using the plurality of controlled magnets to position the guide catheter at a desired location within the fetus. The method also includes introducing a treatment catheter over or in the guide catheter; moving the treatment catheter along the guide catheter to position the treatment catheter at a treatment location; and treating the fetal malformation at the treatment location. The method further comprises removing the treatment catheter; removing the guide catheter; and removing the needle.

According to another illustrative embodiment, a method of treating a heart malformation in a fetus in utero includes using a needle to access an umbilical vein of the fetus proximate the fetus' liver, providing a guide catheter having a magnetic object at a distal end, and positioning the guide catheter into the venous system of the fetus via the needle. The method further includes providing a magnetic guidance system and using the magnetic guidance system to direct the guide catheter into the heart of the fetus at a desired location; and introducing a treatment catheter over the guide catheter. The method also includes moving the treatment catheter along the guide catheter to a treatment position in the fetus' heart and treating the fetal malformation at the treatment location.

According to another illustrative embodiment, a method of fetal cardiac intervention to address hypoplastic left heart syndrome in a fetus includes providing an ultrasonic transducer for observing the fetus, using the ultrasonic transducer to guide introduction of a needle into a vein within the fetus, and inserting a guide catheter through the needle into the vein. The method further includes providing a plurality of controlled magnets operable to guide the magnetic object on the guide catheter in three dimensions to within at least a centimeter and using the plurality of controlled magnets to precisely lead the guide catheter into the right atrium, through the Foramen ovale, into the left atrium, through the left mitral valve into the left ventricle, and turning more than 120 degrees to or through the aortic valve. The method also includes introducing a treatment catheter in the form of a balloon catheter onto the guide catheter, moving the treatment catheter along the guide catheter until a balloon portion of the treatment catheter is proximate the fetus' aortic valve, inflating the balloon to dilate the aortic valve, removing the treatment catheter, and removing the guide catheter.

According to still another illustrative embodiment, a system for treating a fetal malformation includes a needle for accessing the fetus' venous system and a guide catheter sized and configured to be introduced into the venous system through the needle. The guide catheter includes a magnetic object on a distal end of the guide catheter. The system also includes a controlled magnet subsystem for moving the magnetic object on the guide catheter within the venous system and into the cardiovascular system of the fetus to within at least three millimeters. The system further includes a treatment catheter sized and configured to coordinate with the guide catheter such that the treatment catheter may be guided along the guide catheter to a treatment location proximate the malformation. The treatment catheter includes a treatment device for treating the heart malformation of the fetus in utero.

The approaches herein, among other things, typically provide for precise navigation through the fetal heart and blood vessels with millimeter precision. This new guidance route can be performed by accessing the fetal umbilical vein or hepatic vein or other aspect of the venous system. The new techniques avoid direct puncture of the fetal heart (direct transthoracic puncture).

Embodiments herein may be used to treat fetal diseases including without limitation blocked cardiac valves/structures and rhythm problems such as: evolving hypoplastic left heart syndrome due to aortic valve stenosis; evolving hypoplasia of the right ventricle due to pulmonary valve stenosis; dilation or stenting of restrictive interatrial septum in disease processes where a restrictive or intact interatrial septum can result in significant neonatal morbidity and mortality (for example, hypoplastic left heart syndrome with intact or restrictive atrial septum); and persistent fetal arrhythmia, unresponsive to medical therapy or in the presence of fetal hydrops.

According to one or more embodiments for the first time use a magnetically steerable guide wire, e.g. guide catheter, is used to gain access across the fetal aortic valve in an antegrade fashion (via the right atrium, left atrium, mitral valve, left ventricle and aortic valve). Using such embodiments allows one to gain access to the fetus via the hepatic vein or other aspect of the venous system, rather than via direct cardiac puncture. A balloon catheter may thereby be placed in the aortic or pulmonary valve. Pacing of the atrium may be achieved to terminate an arrhythmia. In at least some embodiments the guide catheter may be navigated through the interatrial septum.

Other features and advantages of the illustrative embodiments will become apparent with reference to the drawings and detailed description that follow.

DETAILED DESCRIPTION OF ILLUSTRATIVE EMBODIMENTS

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

According to an illustrative embodiment, a method of fetal intervention to address a malformation or other condition is provided that includes introducing a guide catheter into an umbilical vein or blood vessel or aspect of the circulation system of a fetus and using controlled magnets to position the guide catheter to a desired location. A treatment catheter is positioned at a treatment location using the guide catheter and then a treatment is administered using the treatment catheter. A number of illustrative, non-limiting methods will be presented.

Figure 1:
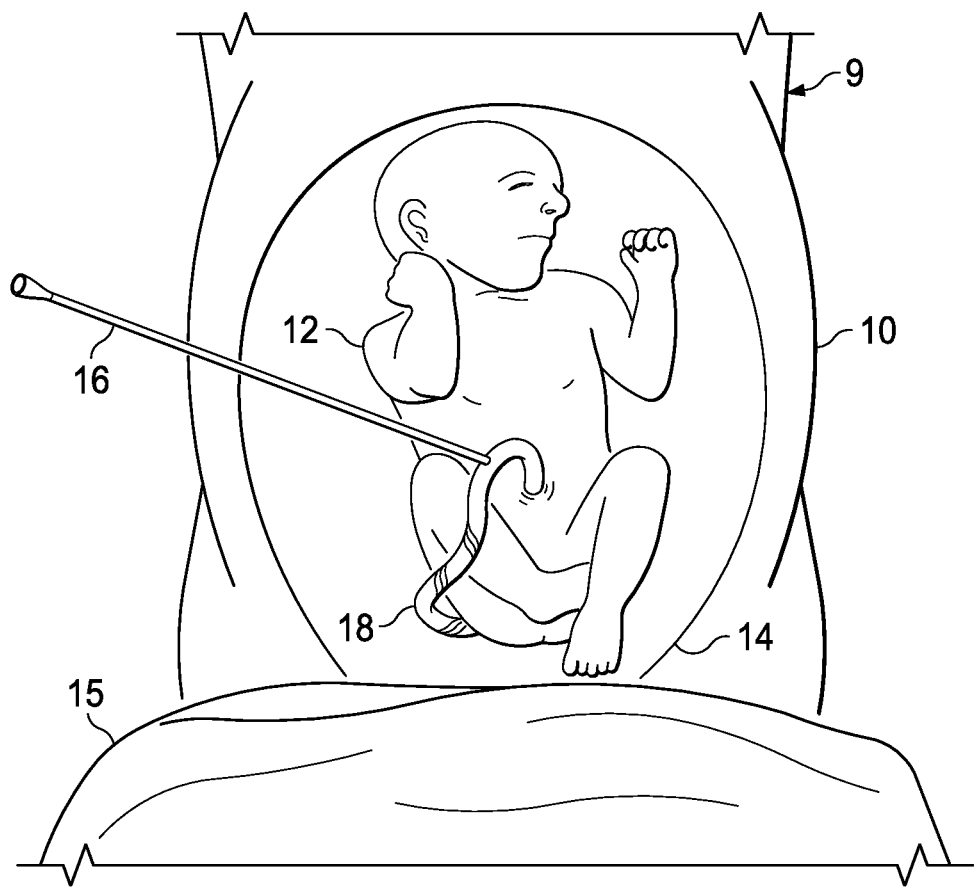
FIG. 1 is a schematic, perspective, anterior view of a pregnant mother's abdomen with a portion removed to show a fetus in the womb.

Referring now primarily to FIG. 1, a schematic, perspective, anterior view of a pregnant mother's 9 abdomen 10 with a portion removed to show a fetus 12 in the womb 14 is presented. A covering 15 covers a portion of the mother 9. A needle 16 is positioned into an umbilical cord 18 of the fetus 12. While "umbilical cord" is used, it should be broadly understood to signify circulation of the infant and thus may be a portion of the liver or umbilical cord proper or any portion of the circulatory system in some embodiments. Thus, the needle 16 may be introduced into the umbilical vein that is in the liver or a hepatic vein or another location to access the venous system. The goal in this regard is typically to access the inferior vena cava. The needle 16 is placed using ultrasonic techniques as is known in the art for in utero procedures. The imaging may be accomplished be via ultrasound. XR fluoroscopy may also be used. As will be explained further below, the needle 16 provides access to the umbilical cord 18 and thereby the cardiovascular system of the fetus 12.

Figure 2:
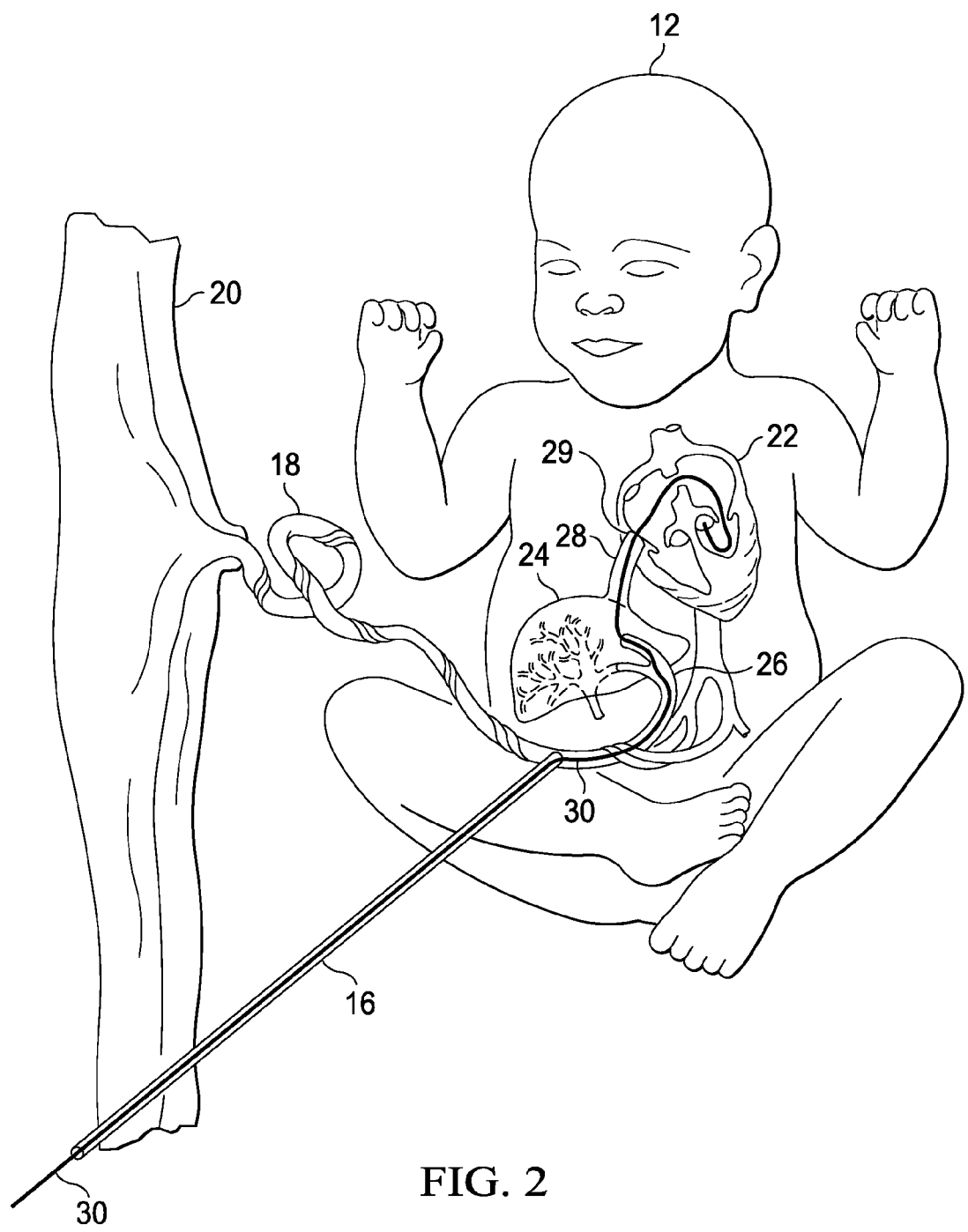
FIG. 2 is a schematic, perspective, anterior view of a fetus in utero with an umbilical cord and with selected internal organs and systems shown.

Referring now primarily to FIG. 2, the fetus 12 is shown in utero with the umbilical cord 18 coupled to placenta 20 of the mother's womb. In this view, certain internal systems of the fetus 12 are shown, e.g., heart 22, liver 24, umbilical vein 26, and ductus venosus 28. A guide catheter 30 is shown disposed in the needle 16. The guide catheter 30 may be a solid wire, tubular device, micro-catheter, or other implement. The guide catheter 30 has been positioned through the umbilical vein 26 and inferior vena cava 29 into the heart 22.

Figure 3:
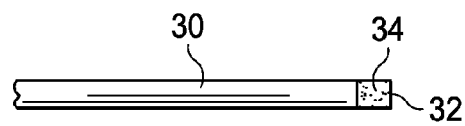
FIG. 3 is a schematic, elevation view of a distal end of a guide catheter according to one illustrative embodiment.

As shown clearly in FIG. 3, a distal end 32 of the guide catheter 30 has a ferromagnetic material or magnetic object 34, e.g., a metal tip or other material that is responsive to a magnetic field. A controlled magnetic field may thus be used to guide the distal end 32 of the guide catheter 30 to a desired position. The controlled magnetic field is developed by a plurality of controlled magnets operable to guide the magnetic object 34 on the guide catheter 30 in three dimensions. For example, an illustrative embodiment of a controlled magnetic system 36 having controlled magnets 38, 40 is shown in FIG. 4.

Figure 4:
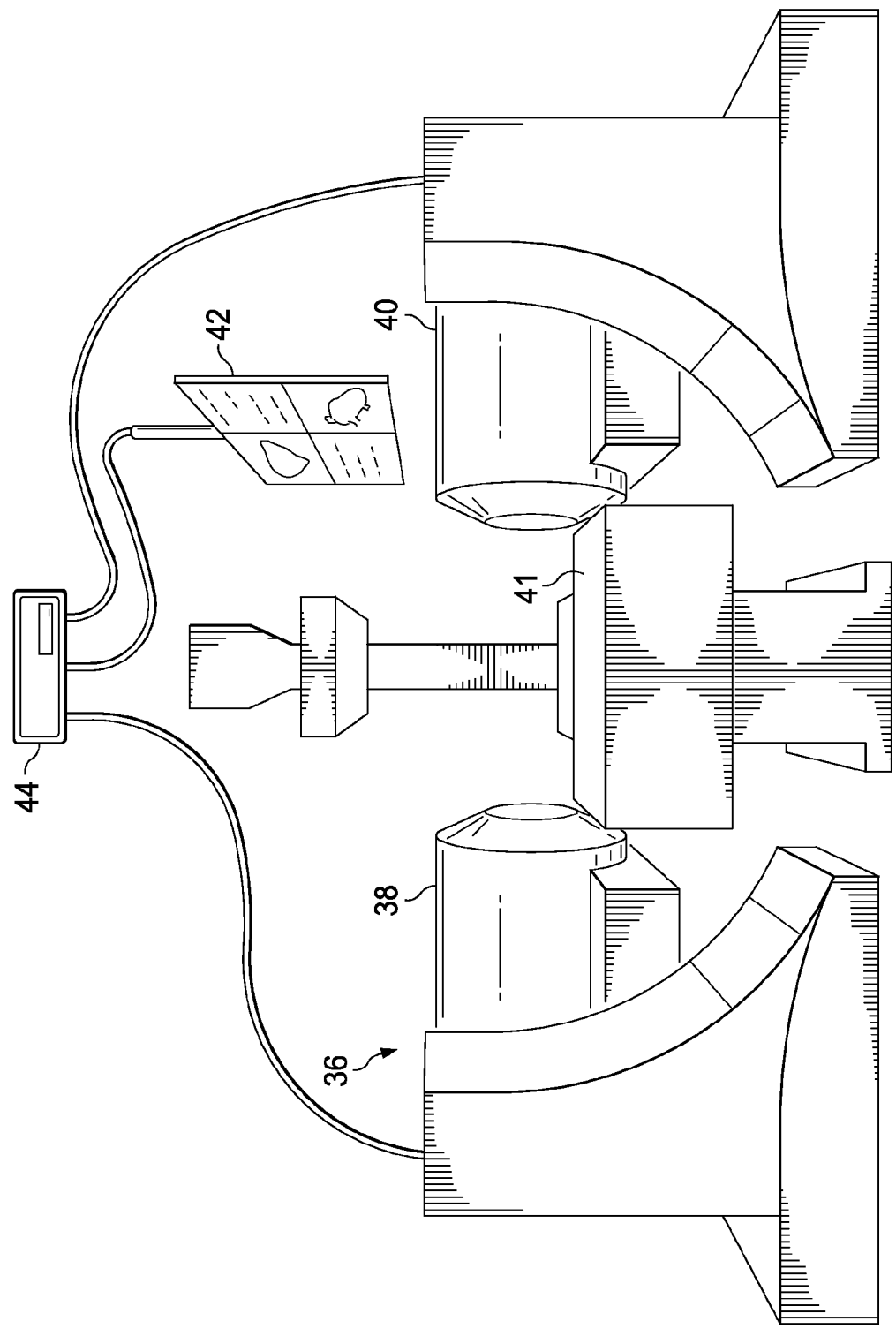
FIG. 4 is a schematic, front, elevation view of an illustrative embodiment of controlled magnets and a treatment bed according to an illustrative embodiment.

Referring now primarily to FIG. 4, the controlled magnetic system 36 includes the plurality of controlled magnets 38, 40, which are controlled by computer 44. The controlled magnetic system 36 may be any system that is capable of moving the magnetic object 34 on the guide catheter 30 in three dimensions to within 1 centimeter, within 50 millimeters or more preferably to within one millimeter (or any encompassed distance). Commercially-available examples of a controlled magnetic system 36 include the magnetic navigation systems available from or developed by Stereotaxis, Inc. of St. Louis, Mo. (www.stereotaxis.com). The controlled magnetic system 36 may include a treatment bed 41 and one more displays 42. The computer 44 is coupled to the controlled magnets 38, 40 and to the display 42 for controlling the magnetic field developed with the magnets 38, 40. By manipulating the position or strength of the controlled magnets 38, 40, the magnetic field may be precisely controlled to develop a three-dimensional force vector on the magnetic object 34 that results in desired movement of the guide catheter 30.

Figure 5:
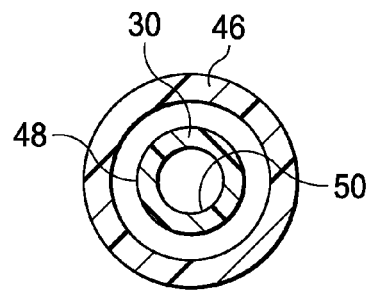
FIG. 5 is a schematic, cross-sectional view of a guide catheter according to one illustrative embodiment.

The controlled magnets 38, 40 are used to guide the magnetic object 34 and thereby the guide catheter 30 to a desired position. After moving the guide catheter 30 or simultaneously therewith a treatment catheter 46 may be guided along the guide catheter 30 to a treatment location; that is, a relevant portion of the treatment catheter 46 is guided to the location where treatment is desired. With reference to FIG. 5, it should be noted that the guide catheter 30 may be a solid guide member, e.g., a wire, or a hollow tubular member and, depending on the type of guide catheter 30 and desired mode of operation, the treatment catheter 46 may be a tubular member that goes over an exterior 48 of the guide catheter 30 or may go into an interior portion 50 of the guide catheter if the guide catheter 30 is tubular. For example, in FIG. 5, the guide catheter 30 is tubular and the treatment catheter 46 is shown on the exterior 48 of the guide catheter 30. It should be understood that any of permeations of these catheters may be utilized to position the treatment catheter 46 at a treatment location.

Figure 6:
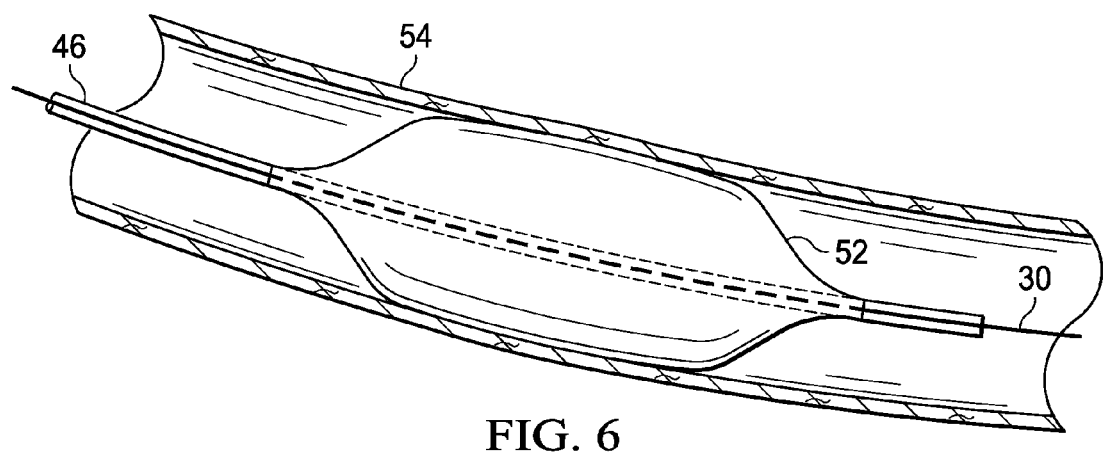
FIG. 6 is a schematic, longitudinal, cross-sectional view of an illustrative embodiment of a treatment catheter in the form of an illustrative balloon catheter shown within a vein or artery.

Depending on the fetal malformation or other condition being treated, the treatment catheter 46 may include a treatment portion or treatment device to provide treatment. As one non-limiting example, the treatment catheter may be a balloon dilator. For example, as shown in FIG. 6, the treatment catheter 46 is shown as a balloon catheter having a portion with an inflatable balloon 52. The treatment catheter 46 with balloon 52 is shown in a vein or artery 54 and over the guide catheter 30, e.g., a wire. In other embodiments, the treatment catheter 46 may include a port for delivering a medicine or agent, such as a coagulant, or may include a pacemaker that may be anchored in at a treatment location. Fetal aortic valve dilation may require a larger balloon annulus ratio for the aortic valve than for newborn aortic valve intervention. The fetal aortic valve behaves quite differently to a newborn aortic valve. There appears to be rapid restenosis at the pulmonary valve and the atrial septum resulting in the need for reintervention. Using embodiments herein, repeat dilations may be accomplished. In still other examples, the treatment catheter 46 may include thermal oblation device, endothermal oblation device, or other device.

It will be appreciated that numerous fetal malformations may be treated with fetal intervention methods and systems described herein. For example, one condition well suited for treatment is a malformation that would otherwise result in hypoplastic left heart syndrome. With this condition, aspects of the left portion of the fetal heart are under developed (hypoplastic). To prevent or ease the condition, a balloon catheter, or balloon dilator, is used as the treatment catheter 46 and is positioned at the aortic valve and expanded to dilate the valve. An illustrative treatment will now be described in more detail.

Application of some illustrative embodiments herein to fetal cardiac intervention procedures may depend on criteria that vary for different procedures. Some non-limiting possible examples follow:

A) Fetal aortic valve dilation involves a fetus with severe aortic stenosis, predicted to progress to Hypoplastic Left Heart Syndrome (flow reversal in the transverse arch). To fulfill these parameters in addition to aortic stenosis, the LV length z score should be >−2. Also typical requirements are for ≤4 of the following: LV length z score >0, LV short axis size z score >0, aortic valve z-score >−3.5, mitral valve z score >−2 and gradient>20 mmHg.

B) For pulmonary valve intervention, the fetus should have severe pulmonary valve stenosis in the presence of an intact ventricular septum resulting in an evolving hypoplastic right heart syndrome. Tricuspid valve z-score <−3 is associated with univentricular neonatal outcome. Fetuses with tricuspid valve z-scores >−3 with severe pulmonary valve stenosis would be considered for pulmonary valve intervention.

C) The presence of a restrictive interatrial septum in patients with congenital heart disease that places them at high neonatal mortality. The interatrial septum < or = to 3 mm in a cardiac lesion requiring interatrial mixing or prevention of left atrial hypertension as documented by fetal pulmonary venous Doppler abnormalities.

D) For arrhythmias that are refractory to medical therapy or presenting in fetal hydrops and cardiac compromise.

Figure 7:
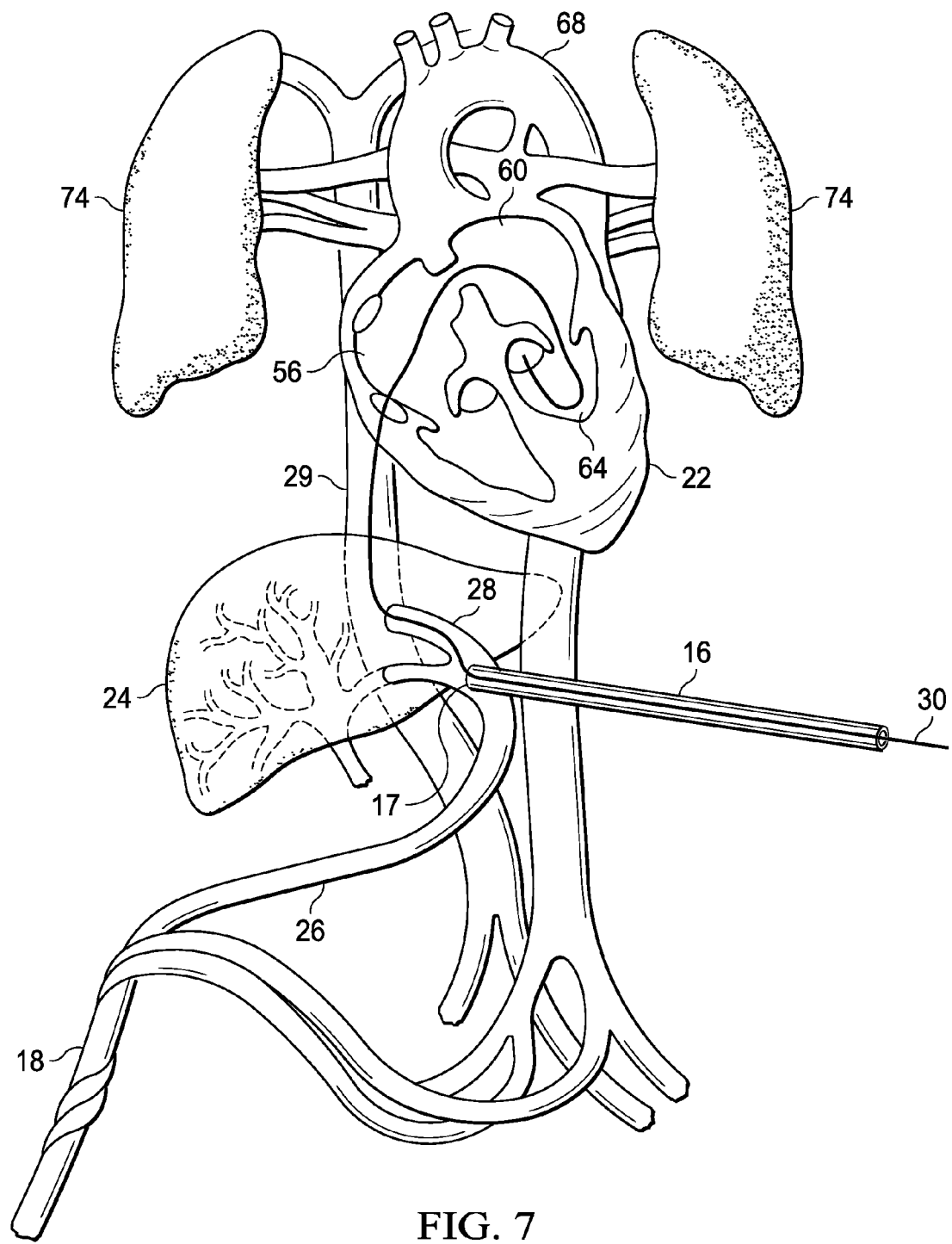
FIG. 7 is a schematic, anterior diagram of the cardiovascular system of a fetus illustrating the position of a guide catheter according to an illustrative embodiment.
Figure 8:
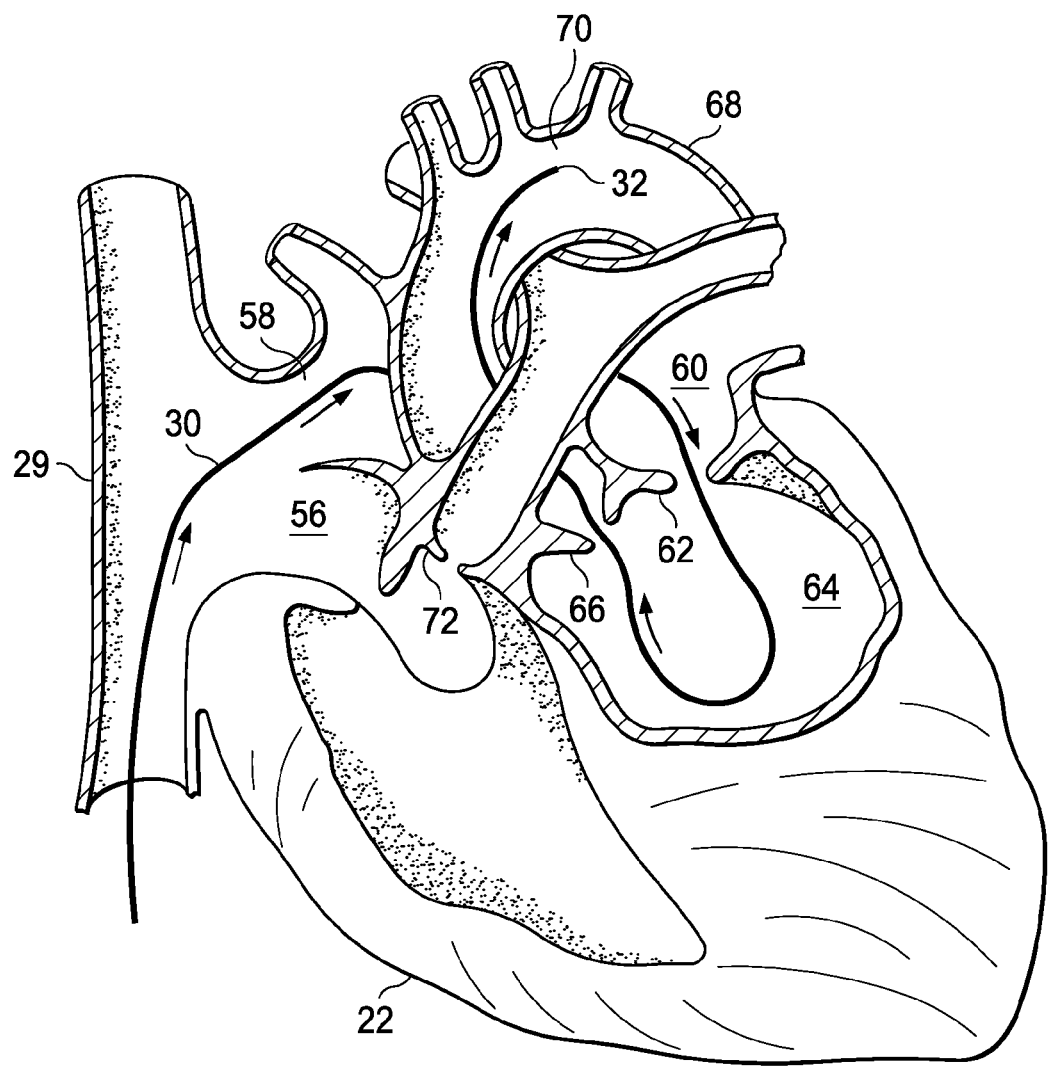
FIG. 8 is a schematic, anterior, sectional view of a fetal heart with a cardiac malformation of the left ventricle and showing one illustrative path for the guide catheter.

Referring now primarily to FIGS. 7 and 8, and initially to FIG. 7, the needle 16 is introduced in utero into the umbilical cord 18, which broadly includes circulation. The healthcare provider uses ultrasound to guide the needle 16 into the umbilical cord 18 or other aspect of the venous system. With this and other treatments, the needle 16 may be introduced into a free-floating portion of the umbilical cord 18 or a portion at or in (i.e., generally proximate or near) the liver 24. In this illustrative method, the needle 16 is shown entering the umbilical cord 18 (specifically the umbilical vein 26) proximate the liver 24. In various embodiments, access may be achieved from a liver vein and not from the umbilicus.

The guide catheter 30 is introduced into the needle 16 until the magnetic object 34, which may be a portion of a solid wire in some embodiments, on the distal end 32 extends out of a distal end 17 of the needle 16. The plurality of controlled magnets 38, 40 of the controlled magnet system 36 is used to guide the distal end 32 of the guide catheter 30. The healthcare provider may be assisted by an engineer or technician that operates the controlled magnet system 36 as requested by the healthcare provider to precisely navigate to a desired location as the healthcare provider monitors with ultrasound. In this illustrative embodiment, the distal end 32 is led through the ductus venosus into the inferior vena cava 29 and into the heart 22. The needle 16 is typically left in place until the guide catheter 30 reaches the heart 22, but the needle 16 could be removed sooner or could remain in place longer including through the duration of the procedure for stability.

Referring now primarily to FIG. 8, at the heart 22, the distal end 32 of the guide catheter 30 is led from inferior vena cava 29 into the right atrium 56 through the Foramen ovale 58 into the left atrium 60. The distal end 32 is led from the left atrium 60 through the left mitral valve 62 into the left ventricle 64. The distal end 32 is then led to the aortic valve 66. In some embodiments, the distal end 32 may be guided through aortic valve 66 and into the aorta 68, e.g., into the aortic arch 70. In such an example, the desired location for the distal end 32 before placing the treatment catheter 46 is the aortic arch 70 but the treatment location is the aortic valve 66. In another embodiment, the desired location for the distal end 32 may the aortic valve 66 and the treatment location may also be the aortic valve 66. While not limiting the approach, it is believed that in many instances locating the distal end 32 in the aortic arch 70 will provide superior stability as the treatment catheter 46 is guided to the aortic valve 66. It should be noted that the distal end 32 is led to make a significant change of direction while in the left atrium 64. For example, the distal end 32 of the guide catheter 30 may turn more than 120 degrees and may turn all the way 180 degrees as suggested in FIG. 8.

With the distal end 32 of the treatment catheter 30 in a desired location, the treatment catheter 46 may be guided along the guide catheter 30. In other embodiments, the guide catheter and treatment catheter 46 could be combined and moved simultaneously. Typically, the treatment catheter 46 is positioned after positioning the guide catheter 30 and the treatment catheter 46 is moved using physical force supplied by the healthcare provider. The treatment catheter 46 is guided along the guide catheter 30 until the distal end or a treatment device or portion is proximate the treatment location, i.e., the aortic valve in this example. In this instance, the treatment catheter 46 is a balloon catheter and the balloon 52 (FIG. 6) is positioned at the treatment location and temporarily inflated. The balloon 52 may include a radiopaque marker, and x-ray may be used to verify the location of the balloon 52 in the aortic valve 66 prior to inflation. The inflation dilates the aortic valve 66 and thereby improves its function.

After treating the aortic valve 66, the treatment catheter 46 and guide catheter 30 are removed from the fetus and the mother. As noted earlier, the needle 16 may be removed at any time after the guide catheter 30 is introduced.

It should be understood that analogous procedure may be used to position the guide catheter 30 (and the treatment catheter 46) at or proximate the pulmonary valve 72 or any other desired treatment location in the cardiovascular system. In another procedure, the guide catheter 30 is guided through the aorta 68 and into a lung 74 or through the pulmonary valve into the pulmonary artery or across the intra atrial septum into the left atrium.

According to another illustrative embodiment, a method for fetal intervention includes treating a stenotic pulmonary valve. The method is analogous to those previously presented except the plurality of controlled magnets 38, 40 are used to position the guide catheter 30 at or near the pulmonary valve 72 of the fetus 12. The treatment catheter 46 is a balloon catheter that is positioned at the pulmonary valve 72. The balloon on the balloon catheter is temporarily inflated to expand the pulmonary valve 72.

According to another illustrative embodiment, a method for fetal intervention includes treating cystic adenomatoid malformation. The plurality of controlled magnets 38, 40 is used to position the guide catheter 30 at a desired location within the fetus 12, and in particular to position the guide catheter 30 through the pulmonary valve 72 of the fetus and into the tumor. The usual step of introducing a treatment catheter 46 over or in the guide catheter 30 includes introducing a delivery catheter over guide catheter. The delivery catheter is sized and configured to deliver a liquid or other fluid to the treatment location. The method further includes delivering a coagulant, including coagulant coils or beads, through the treatment catheter 46 to the tumor.

According to another illustrative embodiment, a method for fetal intervention includes treating a Bradycardia heart in a fetus. According to this embodiment, the plurality of controlled magnets is used to position the guide catheter at a desired location within the fetus. This step includes positioning the guide catheter into the ventricle of the fetus. A catheter with a pacemaker releaseably coupled proximate the distal end is presented. The treatment catheter is guided so that the pacemaker is proximate the treatment location and the pacemaker is released. The fetal malformation at the treatment location is treated by activating the pacemaker. In one embodiment, a wire is placed in contact with the endocardial surface to transmit the electronic impulse from the external pacemaker to the ventricle.

Figure 9:
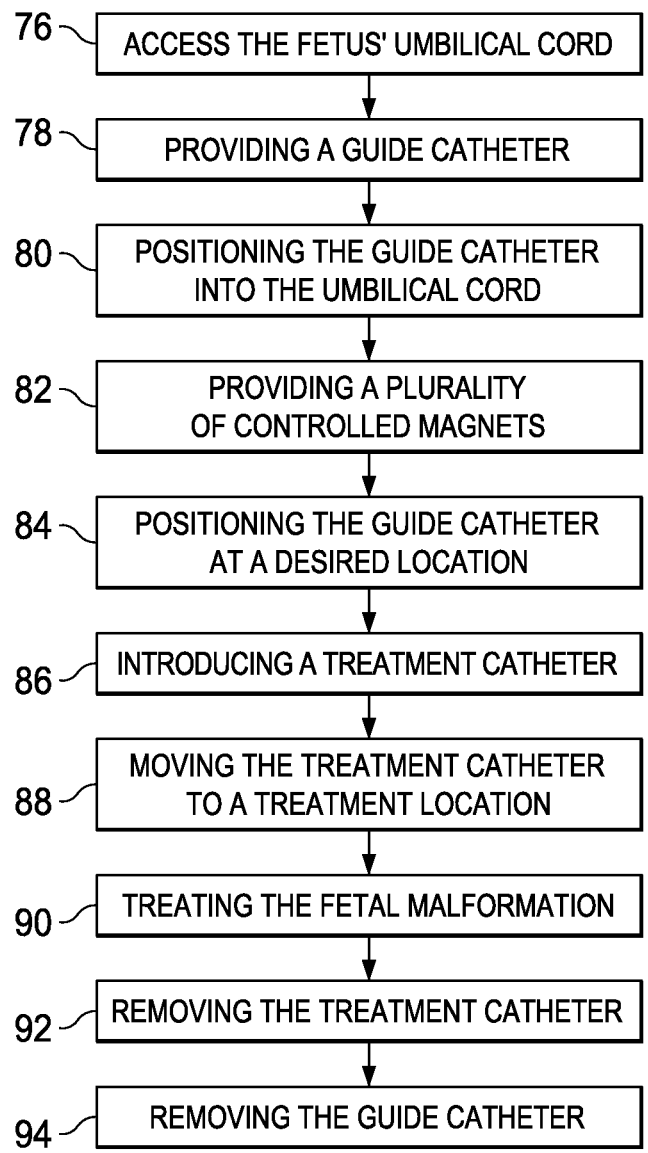
FIG. 9 is a flow chart showing an illustrative embodiment of a method for addressing a fetal malformation in a fetus in utero through fetal intervention.

Referring now primarily to FIG. 9, an illustrative method for addressing a fetal malformation in a fetus in utero through fetal intervention is presented as a process flow. The method begins at step 76 with accessing the fetus' umbilical cord. At step 78, a guide catheter having a magnetic object coupled proximate a distal end of the guide catheter is provided. At step 80, the guide catheter is positioned or guided into the umbilical cord of the fetus through the needle. At step 82, a plurality of controlled magnets operable to guide the magnetic object on the guide catheter in three dimensions to within at least a centimeter and preferably within one millimeter is provided. At step 84, the plurality of controlled magnets is used to position the guide catheter at a desired location within the fetus.

At step 86, a treatment catheter is introduced over or into the guide catheter. At step 88, the treatment catheter is guided along the guide catheter to position the treatment catheter at a treatment location. At step 90, the fetal malformation is treated using the treatment catheter at the treatment location. At step 92, the treatment catheter is removed, and at step 94 the guide catheter is removed. While these steps are shown sequentially, it should be understood that the order may be modified or steps combined for many of the steps.

In one illustrative embodiment, the procedure steps include: Access the fetus' circulation; position the needle into the circulation; provide the controlling magnets; advance a guide wire through the needle into the circulation and with the magnets; direct the wire to a treatment location; introduce the treatment catheter over the guide wire (guide catheter); move treatment catheter to treatment location over the guide wire; treat the malformation; remove the needle; remove the treatment catheter; and remove the wire. In one illustrative embodiment, the magnetic guided wire may provide the treatment by creation of defect (radiofrequency perforation) or pacing.

Figure 10:
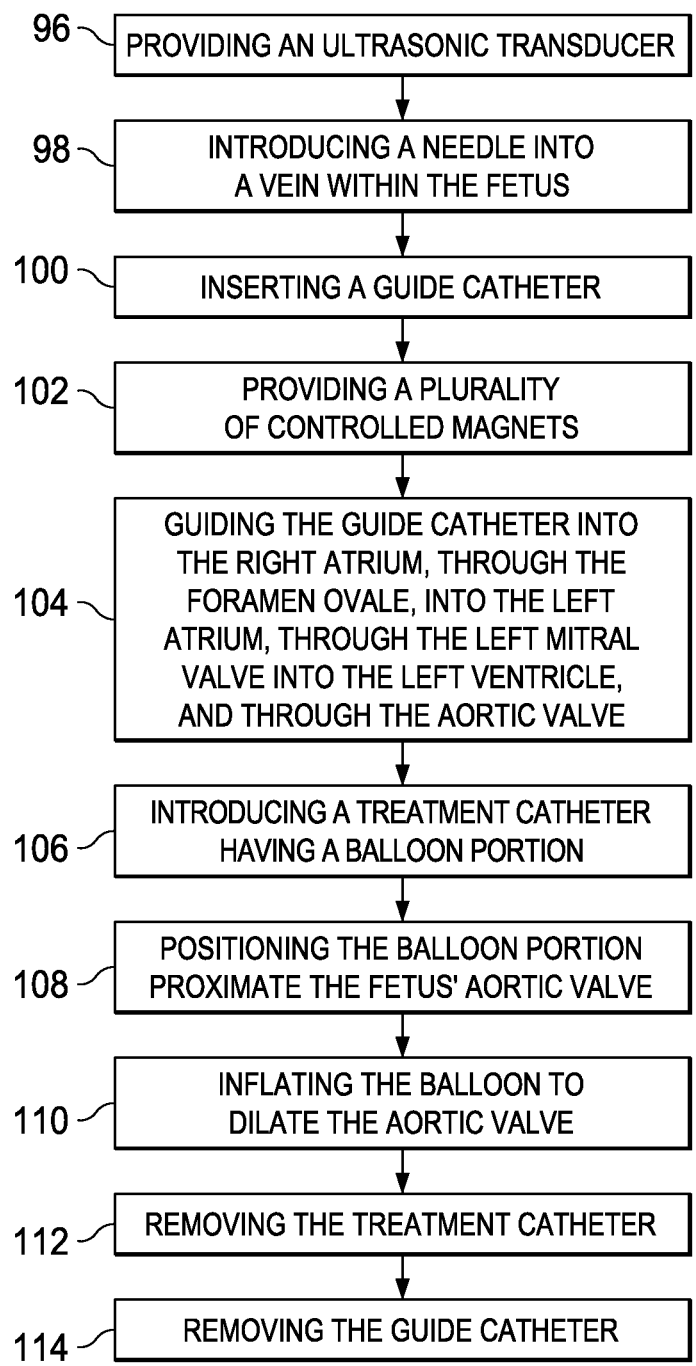
FIG. 10 is a flow chart showing an illustrative embodiment of a method for addressing a fetal malformation in a fetus in utero through fetal intervention.

Referring now primarily to FIG. 10, an illustrative method of fetal cardiac intervention to address hypoplastic left heart syndrome in a fetus is presented as a process flow. The process begins at step 96 with providing an ultrasonic transducer for observing the fetus. At step 98, the ultrasonic transducer is used to guide the introduction of a needle into a vein within the fetus. At step 100, a guide catheter is inserted through the needle into the vein. At step 102, a plurality of controlled magnets capable of moving the magnetic object on the guide catheter in three dimensions to within at least one centimeter millimeters or preferably within three millimeters or still more preferably within one millimeter is provided. At step 104, the plurality of controlled magnets is used to precisely lead the guide catheter into the right atrium, through the Foramen ovale, into the left atrium, through the mitral valve into the left ventricle, and turning more than 120 degrees—typically about a 180 degrees—through the aortic valve. At step 106, a treatment catheter in the form of a balloon catheter is introduced onto the guide catheter. It should be noted that the guide catheter and treatment catheter could be an integral unit and moved simultaneously. At step 108, the treatment catheter is guided along the guide catheter until a balloon portion of the treatment catheter is proximate the fetus' aortic valve.

At step 110, the balloon is temporarily inflated to dilate the aortic valve. At step 112, the treatment catheter is removed. At step 114, the guide catheter is removed. At step 116, the needle is removed. While these steps are shown sequentially, it should be understood that the order may be modified or steps combined for many of the steps.

Illustrative embodiments herein perform cardiac intervention in a fetus with a major cardiac defect using a magnetic navigation technique. Embodiments of some of the methods include steps wherein a guidewire is inserted through a trocar needle into the hepatic vein or the umbilical vein or other aspect of the venous system and guided to the fetal heart. Then by magnets the wire is guided from the right atrium to the left atrium, to the left ventricle, around the apex of the left ventricle to the aortic valve, to the ascending aorta, to the descending aorta, and placed across the aortic valve. A balloon catheter is then advanced over the wire to a position across the aortic valve. Then the balloon is inflated to perform an aortic valve dilation. This improvement is less invasive than the current prior art protocols involving direct cardiac puncture of the fetus.

Various illustrative, non-limiting embodiments of the methods herein may include some or all of the following steps in this or a different order:

Perform an ultrasound displaying the fetal position.
Reposition the fetus if necessary.
When fetal position is satisfactory, place the mother under general anesthesia.
Administer additional fetal anesthesia either via the intramuscular route, umbilical vein, or directly into the hepatic vein with the initial puncture.
With the mother under general anesthesia, prepare and drape the abdomen in a sterile fashion.
With ultrasound guidance, insert a Cook trocar and needle in the hepatic vein or the umbilical vein.
Remove the trocar.

Advance a 0.014" magnetic guidewire (i.e., an illustrative guide catheter) via the needle through the hepatic vein to the fetal heart.

Turn on the stereotaxis magnetic fields.

Guide the wire to the location of interest to perform the procedure of interest. For example, the most common intervention is aortic valve dilation and the wire/guide catheter is guided to the aortic valve to be dilated. Other proceedings have other locations of interest to which the wire (e.g., the guide catheter) is guided.

Under ultrasound visualization, direct the wire with magnets from the right atrium, to the left atrium, to the left ventricle, around the apex of the left ventricle to the aortic valve, to the ascending aorta, and then to the descending aorta.

With the wire across the aortic valve and the magnets still engaged, advance a balloon catheter measuring 1 to 1.2 times the size of the aortic annulus over the wire.

Brief fluoroscopy may be desired at this time to confirm the balloon position (with estimated total fluoroscopy time of less than one minute).

Inflate the balloon under ultrasound visualization.

Repeat inflations may be necessary.

Once the treatment is completed, the wire, balloon and needle (if not already removed) are withdrawn.

The status of the fetus is monitored by ultrasound.

The mother is awakened from anesthesia.

The fetus and mother are closely monitored after the procedure.

The embodiments herein offer improvements. Some of the possible improvements are listed here. By utilizing access some distance from the chest there is no ultrasound interference from the introducer. The problems associated with other techniques such as fetal position, wire manipulation, and balloon delivery, should be minimized. In fact, the fetal position likely to be the most challenging with this technique is when the left side of the chest is close to the maternal abdomen. Therefore, a combination of both invasive and noninvasive techniques may be necessary to perform the procedure without maternal open laparotomy, in such cases.

According to one illustrative method of fetal cardiac intervention using magnetically guided navigation, the steps include: performing an ultrasound displaying the fetal position; repositioning the fetus as necessary; when fetal position is satisfactory, placing the mother under general anesthesia; administering additional fetal anesthesia either via the intramuscular route, umbilical vein, or directly into the hepatic vein with the initial puncture; with the mother under general anesthesia, preparing and draping the abdomen in a sterile fashion; with ultrasound guidance, inserting a trocar and needle in the hepatic vein or the umbilical vein; removing the trocar; advancing a magnetic guidewire via the needle through the hepatic vein or the umbilical vein to the fetal heart; turning on the stereotaxis magnetic fields; under ultrasound visualization, directing the wire with magnets from the right atrium, to the left atrium, to the left ventricle, around the apex of the left ventricle to the aortic valve, to the ascending aorta, and then to the descending aorta; placing the wire across the aortic valve; with the wire across the aortic valve and the magnets still engaged, advancing a balloon catheter measuring 1 to 1.2 times the size of the aortic annulus over the wire; performing a brief fluoroscopy to confirm the balloon position; inflating the balloon under ultrasound visualization; repeating inflations as necessary; once the treatment is completed, withdrawing the wire, balloon and needle; monitoring by ultrasound the status of the fetus; awakening the mother from anesthesia; and closely monitoring the fetus and mother.

According to another illustrative, non-limiting embodiment, a method of fetal cardiac intervention using magnetically guided navigation includes the steps of: performing an ultrasound displaying the fetal position; repositioning the fetus as necessary; when fetal position is satisfactory, placing the mother under general anesthesia; administering additional fetal anesthesia either via the intramuscular route, umbilical vein, or directly into the hepatic vein with the initial puncture; with the mother under general anesthesia, preparing and draping the abdomen in a sterile fashion; with ultrasound guidance, inserting a trocar and needle in the hepatic vein or the umbilical vein; removing the trocar; advancing a magnetic guidewire via the needle through the hepatic vein or the umbilical vein to the fetal heart; turning on the stereotaxis magnetic fields; performing a fetal cardiac intervention procedure; monitoring by ultrasound the status of the fetus; awakening the mother from anesthesia; and closely monitoring the fetus and mother. In one illustrative embodiment, the fetal cardiac intervention procedure may include the following steps: under ultrasound visualization, directing the wire with magnets from the right atrium, to the left atrium, to the left ventricle, around the apex of the left ventricle to the aortic valve, to the ascending aorta, and then to the descending aorta; placing the wire across the aortic valve; with the wire across the aortic valve and the magnets still engaged, advancing a balloon catheter measuring 1 to 1.2 times the size of the aortic annulus over the wire; performing a brief fluoroscopy to confirm the balloon position; inflating the balloon under ultrasound visualization; repeating inflations as necessary; and once the treatment is completed, withdrawing the wire, balloon and needle. In one or more embodiments, the fetal cardiac intervention procedure may be a member of the group comprising: fetal cardiac valve dilation; pulmonary valve dilation; restrictive interatrial septum procedures; and procedures for arrhythmias.

According to some embodiments, methods are shown herein for fetal cardiac intervention using magnetically guided intervention, wherein a guidewire is inserted through a trocar needle into the hepatic vein or the umbilical vein and guided to the fetal heart. Then by magnets the wire is guided from the right atrium to the left atrium, to the left ventricle, around the apex of the left ventricle to the aortic valve, to the ascending aorta, to the descending aorta, and placed across the aortic valve. A balloon catheter is then advanced over the wire to a position across the aortic valve. Then the balloon is inflated to perform an aortic valve dilation Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in connection to any one embodiment may also be applicable to any other embodiment.

It will be understood that the benefits and advantages described above may relate to one embodiment or may relate to several embodiments. It will further be understood that reference to "an" item refers to one or more of those items.

The steps of the methods described herein may be carried out in any suitable order, or simultaneously where appropriate.

Where appropriate, aspects of any of the examples described above may be combined with aspects of any of the other examples described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. A method for addressing a fetal malformation in a fetus in utero through fetal intervention, the method comprising: using a needle to access the fetus' umbilical cord; providing a guide catheter having a magnetic object coupled proximate a distal end of the guide catheter; positioning the guide catheter into the umbilical cord of the fetus through the needle; providing a plurality of controlled magnets operable to guide the magnetic object on the guide catheter in three dimensions to within at least a centimeter; using the plurality of controlled magnets to guide the guide catheter from an access point of the umbilical cord to a desired location within the fetus' heart; introducing a treatment catheter over or in the guide catheter; moving the treatment catheter along the guide catheter to position the treatment catheter at a treatment location; treating the fetal malformation at the treatment location; removing the treatment catheter; removing the guide catheter; and removing the needle.

2. The method of claim 1, wherein the step of using a needle to access the fetus' umbilical cord comprises placing the needle into the umbilical cord proximate the fetus' liver.

3. The method of claim 1, wherein the step of using a needle to access the fetus' umbilical cord comprises placing the needle into the umbilical cord at a free floating location.

4. The method of claim 1, wherein: the fetal malformation is a hypoplastic left heart; the step of using the plurality of controlled magnets to guide the guide catheter to a desired location within the fetus' heart comprises positioning the guide catheter into the fetus' aorta; the step of introducing a treatment catheter over or in the guide catheter comprises introducing a balloon catheter over the treatment catheter; the step of moving the treatment catheter along the guide catheter comprises moving the balloon catheter until the balloon catheter is proximate the aortic valve; and the step of treating the fetal malformation at the treatment location comprises inflating a balloon of the balloon catheter to expand the fetus' aortic valve.

5. The method of claim 1, wherein: the fetal malformation is a stenotic pulmonary valve; the step of using the plurality of controlled magnets to guide the guide catheter to a desired location within the fetus' heart comprises positioning the guide catheter into the pulmonary valve of the fetus; the step of introducing a treatment catheter over or in the guide catheter comprises introducing a balloon catheter over the treatment catheter; the step of moving the treatment catheter along the guide catheter comprises moving the balloon catheter until the balloon catheter is proximate the pulmonary valve; and the step of treating the fetal malformation at the treatment location comprises inflating a balloon of the balloon catheter to expand the fetus' pulmonary valve.

6. The method of claim 1, wherein the fetal malformation is a congenital cystic adenomatoid malformation having a tumor; the step of using the plurality of controlled magnets to guide the guide catheter to a desired location within the fetus' heart comprises positioning the guide catheter through the pulmonary artery of the fetus and into the tumor; the step of introducing a treatment catheter over or in the guide catheter comprises introducing a delivery catheter over guide catheter; the step of moving the treatment catheter along the guide catheter comprises moving the treatment until the treatment catheter is proximate the tumor; and the step of treating the fetal malformation at the treatment location comprises delivering a coagulant through the treatment catheter to the tumor.

7. The method of claim 1, wherein: the fetal malformation is a Bradycardia heart; the step of using the plurality of controlled magnets to guide the guide catheter to a desired location within the fetus' heart comprises positioning the guide catheter into a ventricle of the fetus; the step of introducing a treatment catheter over or in the guide catheter comprises introducing a catheter with a pacemaker releasably coupled proximate the distal end; the step of moving the treatment catheter along the guide catheter comprises moving the treatment catheter so that the pacemaker is proximate the treatment location and releasing the pacemaker; and the step of treating the fetal malformation at the treatment location comprises activating the pacemaker.

8. The method of claim 1, wherein providing a guide catheter comprises providing a solid guide line and the step of introducing a treatment catheter comprises introducing the treatment catheter over the guide catheter.

9. The method of claim 1, wherein providing a guide catheter comprises providing a tubular guide line and the step of introducing a treatment catheter comprises introducing the treatment catheter into the tubular guide line.

10. The method of claim 1, wherein: the step of using a needle to access the fetus' umbilical cord comprises placing the needle into the umbilical cord proximate the fetus' liver; the fetal malformation is a hypoplastic left heart; the step of using the plurality of controlled magnets to guide the guide catheter to a desired location within the fetus comprises positioning the guide catheter into the aorta of the fetus; the step of introducing a treatment catheter over or in the guide catheter comprises introducing a balloon catheter over the treatment catheter; the step of moving the treatment catheter along the guide catheter comprises moving the balloon catheter until the balloon catheter is proximate the aortic valve; and the step of treating the fetal malformation at the treatment location comprises inflating a balloon of the balloon catheter to expand the fetus' aortic valve.

11. A method of treating a heart malformation in a fetus in utero, the method comprising: using a needle to access an umbilical vein of the fetus proximate the fetus' liver; providing a guide catheter having a magnetic object proximate a distal end; positioning the guide catheter into the umbilical vein of the fetus via the needle; providing a magnetic guidance system; using the magnetic guidance system to direct the guide catheter from an entry location of the umbilical vein into the heart of the fetus at a desired location; moving a treatment catheter to a treatment position in the fetus' heart; and treating the fetal malformation at the treatment location.

12. The method of claim 11, wherein: the heart malformation is a hypoplastic left heart syndrome; the step of using the magnetic guidance system to direct the guide catheter from an entry location of the umbilical vein into the heart of the fetus to a desired location comprises directing the guide catheter into the aorta of the fetus; the step of moving the treatment catheter to a treatment position comprises moving the treatment catheter proximate the aortic valve; the treatment catheter comprises a balloon catheter; and the step of treating the fetal malformation comprises activating the balloon catheter to expand the aortic valve.

13. The method of claim 11 comprising;
providing an ultrasonic transducer for observing the fetus;
using the ultrasonic transducer to guide introduction of a needle into umbilical vein within the fetus;
using the plurality of controlled magnets to lead the guide catheter into the right atrium, through the Foramen ovale, into the left atrium, through the left mitral valve into the left ventricle, and turning more than 120 degrees to or through the aortic valve;
introducing the treatment catheter in the form of a balloon catheter onto the guide catheter;
moving the treatment catheter along the guide catheter until a balloon portion of the treatment catheter is proximate the fetus' aortic valve;
inflating the balloon to dilate the aortic valve to treat the fetus' heart;
removing the treatment catheter; and
removing the guide catheter.

14. The method of claim 13, wherein the step of using a plurality of controlled magnets further includes leading the guide catheter to the aortic arch.

15. The method of claim 13, further comprising using radiography to verify the location of the balloon before inflating the balloon.

* * * * *